| United States Patent [19] | [11] Patent Number: 4,778,824 |
| Umezawa et al. | [45] Date of Patent: Oct. 18, 1988 |

[54] METHOD FOR SUPPRESSING A TRANSPLANTATION IMMUNITY AND TREATING AN ALLERGIC DISEASE AND AN AUTOIMMUNE DISEASE

[75] Inventors: Hamao Umezawa; Tomio Takeuchi; Masaaki Ishizuka; Fuminori Abe, all of Tokyo; Akio Fujii, Kamakura; Teruya Nakamura, Kusatsu, all of Japan

[73] Assignee: Zaidan Hojin Biseibutsu Kagaku Kenkyu Kai, Tokyo, Japan

[21] Appl. No.: 65,613

[22] Filed: Jun. 30, 1987

Related U.S. Application Data

[63] Continuation of Ser. No. 799,575, Nov. 19, 1985, abandoned.

[30] Foreign Application Priority Data

Dec. 6, 1984 [JP] Japan ................................ 59-256476

[51] Int. Cl.$^4$ .............................................. A61K 31/16
[52] U.S. Cl. .................................... 514/626; 514/613; 514/885; 564/147
[58] Field of Search ...................... 514/18, 21, 19, 20, 514/147, 885–887, 814, 613, 626

[56] References Cited

FOREIGN PATENT DOCUMENTS 2084999  4/1982  United Kingdom .

OTHER PUBLICATIONS

Umezawa, *Proceedings 13th International Congress of Chemotherapy*, 28th, Aug. to 2nd Sep., Vienna, 1983, pp. 1/76–1/77.
Theofilopoulos in *Basic and Clinical Immunology*, ed. by Stites, 5th Ed., Lange Medical Publication, Los Altos, Calif., 1984, p. 169.
*Chemical Abstracts*, vol. 102, No. 17, 1985, p. 28, abst. No. 142907z.

*Primary Examiner*—J. R. Brown
*Assistant Examiner*—F. T. Moezie
*Attorney, Agent, or Firm*—Henry C. Nields

[57] ABSTRACT

This invention relates to method for suppressing a transplantation immunity and treating an allergic disease and an autoimmune disease in a mammal which comprises administering spergualin or a pharmaceutically acceptable salt thereof in effective amount to the said mammal.

4 Claims, No Drawings

METHOD FOR SUPPRESSING A TRANSPLANTATION IMMUNITY AND TREATING AN ALLERGIC DISEASE AND AN AUTOIMMUNE DISEASE

This application is a continuation of application Ser. No. 799,575, filed Nov. 19, 1985, now abandoned.

BACKGROUND OF THE INVENTION

Various immunosuppressants are currently used in order to suppress rejections and other transplantation immunity reactions that may occur in organ transplantation, and among such suppressive agents are steroid hormones, antimetabolites, alkylating agents and antibiotics. Steroid hormones are effective against a wide variety of allergic diseases, whereas non-steroidal anti-inflammatory agents and anti-inflammatory enzymes are commonly used in symptomatic therapy of inflammations that accompany allergic reactions. Gold compounds and chloroquines are used expressly against rheumatoid arthritis. For the treatment of bronchial asthma and unticaria, anti-histamine ae used.

Existing immunosuppressants generally cause serious side effects when they are administered to humans. It is therefore desired to develop immunosuppressive drugs that act selectively on lymphocytes and other cells of immdnological importance while causing minimum side effects.

On the other hand, in order to cope with the increasing incidence of allergic diseases such as allergic asthma, allergic rhinitis and pollinoala, the development of effective antiallergic agents is desired.

Spergualin is a compound that was isolated by Umezawa, one of the inventors of the present invention, and other from the filtrate of a culture broth of Spergualin-producing microorganism of the genus Bacillus (see Japanese Patent Public Disclosure No. 48957/1982).

SUMMARY OF THE INVENTION

This invention relates to method for suppressing a transplantation immunity and treating an allergic disease and an autoimmune disease in a mammal including human which comprises administering Spergualin or a pharmaceutically acceptable salt thereof in effective amount to the said animal.

Examples of auto-immune disease are an aplastic anemia, an allergic encephalomyelitis and chronic rheumatoid arthritis Type I diabetic syndrome, Systemic lupus exythematosus, etc.

Spergualin is represented by the general formula (I) and may be prepared by a known method (see Japanese Patent Public Disclosure No. 48957/1982):

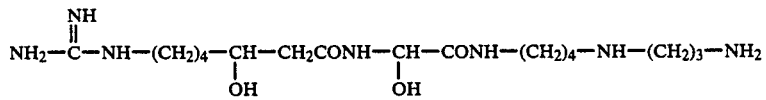

(I)

Spergualin forms salts with acids and from a stability viewpoint, the compound is actually used in the form of its salts. Salt-forming acids may be inorganic or organic if they are pharmaceutically acceptable. Preferred inorganic salts are hydrochloric acid, sulfuric acid, nitric acid and phosphoric acid; preferred organic acids include acetic acid, propionic acid, succinic acid, fumaric acid, maleic acid, malic acid, tartaric acid, glutaric acid, citric acid, benzenesulfonic acid, toluenesulfonic acid, methanesulfonic acid, ethanesulfonic acid, propanesulfonic acid, aspartic acid, glutamic acid and sulfamic acid.

Spergualin may be directly used as an immunosuppressant or anti-allergic agent, but it is usually administered in admixture with excipients or carriers. Pharmaceutically acceptable excipients and carriers should be selected and their type and composition are determined by the route and method of administration. Liquid carriers suitable for preparing injections include water, alcohols, as well as animal, vegetable and synthetic oils such as soybean oil, peanut oil, sesame oil and mineral oil. The following liquid carriers are generally preferred: physiological saline, buffer solutions, sugars such as glucose, mannose and mannitol, aqueous solutions containig cyclitols such as sugar alcohol and inositol, and glycols such as ethylene glycol, propylene glycol and polyethylene glycol. Alternatively, spergualin may be freeze-dried together with excipients such as sugars (e.g. glucose, maltose, sucrose and mannose), sugar alcohols (e.g. mannitol), cyclitols (e.g. cyclic sugar alcohol and inositol) and aminoacids (e.g. phenylalanine). Before intravenous injection, such freeze-dried compound is dissolved in suitable solvents such as sterilized water, physiological saline, glucose solution, electrolyte solution and amino acid solution. With injections, the content of the effective ingredient generally ranges from 0.1 to 30 wt%, preferably from 1 to 10 wt%. For oral administration, the compound of the present invention may be used in the form of tablets, capsules, powders, granules, liquids or dry syrups. With capsules, tablets and powders, the content of the effective ingredient ranges generally from 5 to 100 wt%, preferably from 25 to 100 wt%.

The dosage of the drug containing spergualin as the effective ingredient should be properly determined depending upon the age and body weight of the patient, as well as the severity and type of the disease. The effective dose generally ranges from 1 to 100 mg/kg.day for parenteral administration, and from 5 to 500 mg/kg.day for oral administration.

Acute toxicity tests in mice showed that the $LD_{50}$ of spergualin was approximately 150 mg/kg for intraperitoneal administration and that the gradual intravenous administration of 80 mg/kg was not lethal. No cumulative toxicity was observed. With these data taken together, supergualine is considered to offer a highly safe drug (Takeuchi et al., Journal of Antibiotics, vol. 34, No. 12, pp. 1619–1621, 1981).

DETAILED DESCRIPTION OF THE INVENTION

The present inventors conducted tests to evaluate the actions of spergualin against the reaction of lymphocyte blastogenesis in accordance with the method of Waithe et al. (Waithe et al., Handbook of Experimental Immunology, page 26.1, 1978). The tests revealed that spergualin inhibited appeciably the T-lymphocyte blast genesis stimulated by concanavalin A (ConA) and the reaction of B-lymphocyte blastogenesis stimulated by lipopolysaccharide (LPS) (Experiments 1 and 2).

Additionally, in accordance with the method of Jerne et al. (Jerne et al., Cell-bound Antibodies, pp. 109-122, 1963), the inventors examined the inhibitory action of spergualin on humoral immunity which is primarily the domain of the B-lymphocytes. The test procedure consisted of counting the number of spleen cells that were extracted from mice sensitized by antigenic sheep red blood cells and which formed immunoglobulin M (IgM) plaques. As summarized in Experiment 3, spergualin exhibited strong inhibitory actions. Encouraged by these data which suggest the possibility that spergualin would inhibit general antibody production by the B-lymphocytes, the present inventors proceeded with their studies to examine the inhibition of the B-lymphocyte ability to produce IgG and IgE antibodies. As summarized in Experiments 4 and 5 spergualin inhibited the production of IgG and IgE.

The above results revealed that spergualin has the ability to inhibit the function of B-lymphocytes, hence humoral immunity.

On the basis of these results, the present inventors have reached the idea of using spergualin as the effective ingredient of a transplantation immunosuppressant for inhibiting rejections and other transplantation immunological reactions that may occur in organ transplantation and an antiallergic agent. In order to demonstrate the possibility of using the compound of the present invention in a transplantation immunosuppresant, the inventors administered such compound to mice transplanted with P815 mastocytoma as an allograft and checked for any inhibition of the appearance of allokiller T-lymphocytes in response to the graft. As shown in Experiment 6, when spergualin was administered for nine consecutive days starting on the day after the transplantation, the activity of the allokiller in the spleen cells was significantly inhibited. In the next place, the present inventors conducted a skin graft test with rats. In accordance with the method of Denham et al. (Denham et al., International Archives of Allergy and Applied Immunology, vol. 62, pp. 443-458, 1980), the skin of the tail of SHR rats was peeled and allografted onto Fischer rats. When spergualin was administered intraperitoneally to recipient rats daily, starting on the day after the transplantation, the graft acceptance period for the treated rats was extended significantly in comparison with the untreated group and hence, the compound was found to have an unexpectedly great ability to inhibit rejections due to transplantation immunity (see Experiment 7). No such side effects as bone marrow inhibition were observed. These results show only one example of the utility of spergualin in organ transplantation, which is by no means limited to skin transplantation. The inhibitory action of spergualin on tissue rejections is expected to manifest itself not only in skin transplantation but also in the transplantation of such organs as the kidney, heart, spleen, lung, liver, bone marrow and endocrine organs. The degree of rejection will vary depending upon the type of transplantation, syngeneic, allogeneic or xenogeneic; however, is expected to exhibit its effects in all of these cases and differ only with respect to potency.

On the basis of the data obtained in Experiment 3, 4 and 5 that show the ability of the compound of the present invention to inhibit antibody production, the inventors have come to realize that such compound will be useful in the treatment of many allergic diseases, especially those associated with humoral immunity. The direct causes of allergic diseases differ with the specific type of allergy, but except for delayed type hypersensitivity mediated by sensitized lymphoid cells, all allergic reactions depend on antibody production in response to exogenous and engogenous antigens, and on the resulting antigen/antibody interaction. For example, atopic dermatitis, pollinosis, bronchial asthma and allergic rhinitis are caused by the immediate type allergy which is associated with humoral immunity, and IgE is believed to play some role in this immediate type allergy. As shown in Experiment 5, when the compound of the present invention was administered daily to mice sensitized by egg albumin, the formation of anti-egg albumin IgE antibodies in the blood remained at significantly low levels throughout the treatment. It was also found that the inhibitory action of the compound lasted for a certain time after the administration of the compound ceased. These data show that the compound of the present invention has a strong inhibitory action on IgE-associated type I allergic reaction and that therefore the compound will offer an anti-allergic drug useful in the treatment of those allergic diseases in which IgE is involved. As Experiments 4 and 5 show, the compound of the present invention also have the ability to inhibit the production of IgM and IgG, and therefore, its utility will be expanded to the treatment of allergic diseases caused by type II or III hypersensitive reaction, such as serum sickness and hemolytic diseases of new born due to Rh incompatibility.

The following Experiments are provided by way of further illustrations of the activities of the compound of the present invention.

EXPERIMENT 1

Inhibition of Con A induced reaction of T-lymphocyte blastogenesis by spergualin (trihydrochloride)

Spleen cells from BALB/c mice were distributed among wells in a microplate so that each well contained $2 \times 10^5$ cells/0.2 ml. The compound was added to all wells but one, the latter being used as a control. Con A (5 μg/ml) was added to all the wells and the so prepared cell suspensions were cultivated in a 5% $CO_2$ incubator for 72 hours at 37° C. Eight hours before the completion of the incubation, 1 μCi of $^3$H-thymidine was added to each well and the uptake of the thymidine by the cultured cells was measured with a liquid scintillation counter to estimate the progress of the reaction of T-lymphocyte blastogenesis. The percentage inhibition of the blastogenesis by the test compound was calculated by: $(1 = Bdpm/Adpm) \times 100$ wherein Adpm indicates the uptake count for the addition of only Con A and Bdpm, the count for the addition of both Con A and the test compound.

As Table 1 shows, the test compound in accordance with the present invention exhibited a strong ability to inhibit the Con A induced reaction of T-lymphocyte blastogenesis.

TABLE 1

| Inhibition of Con A-induced reaction of T-lymphocyte blastogenesis by spergualin (trihydrochloride) | | |
|---|---|---|
| Concentration (μg/ml) | $^3$H—thymidine uptake (dpm ± S.D.) | Inhibition (%) |
| control (0) | 129,616 ± 35,477 | 0 |
| compound of the present invention (10) | 30,214 ± 25,033 | 76.7 |
| compound of the present | 788 ± 182 | 99.4 |

TABLE 1-continued

Inhibition of Con A-induced reaction of
T-lymphocyte blastogenesis by spergualin
(trihydrochloride)

| Concentration (μg/ml) | $^3$H—thymidine uptake (dpm ± S.D.) | Inhibition (%) |
|---|---|---|
| invention (100) | | |

EXPERIMENT 2

Inhibition of LPS-induced reaction of B-lymphocyte blastogenesis by spergualin (trihydrochloride)

The uptake of $^3$H-thymidine by B-cell was measured in accordance with the method used in Experiment 1, except that the inducer Con A was replaced by 100 μg/ml of LPS from *E. coli*. The percentage inhibition of blastogenesis by the test compound was also determined by the same method as used in Experiment 1.

As Table 2 shows, spergualin was highly effective in suppressing the LPS-induced B-lymphocyte blastogenesis.

TABLE 2

Inhibition of LPS-induced reaction of
B-lymphocyte blastogenesis by spergualin
(trihydrochloride)

| Concentration (μg/ml) | $^3$H—thymidine uptake (dpm ± S.D.) | Inhibition (%) |
|---|---|---|
| control (0) | 234,356 ± 61,436 | 0 |
| compound of the present invention (10) | 38,842 ± 21,573 | 83.4 |
| compound of the present invention (100) | 396 ± 216 | 99.8 |

EXPERIMENT 3

Inhibition of Production of IgM antibody against Sheep Red Blood Cells by spergualin (trihydrochloride)

CDF 1 mice (6–10 wk old, female) were immunized by intravenous injection of $1 \times 10^8$ sheep red blood cells. The mice were intraperitoneally administered varying doses (see Table 3 below) of the test compound for a period of 3 days starting from the day following the intravenous injection. Four days later, spleen cells were isolated from the mice and the number of IgM plaque-forming cells was counted by a known method (Yata et al.; Gan to Kagaku Ryoho (Cancer and Chemotherapy), vol. 2, pp. 903–908, 1975). The percentage inhibition of IgM antibody production was calculated by $(1-B/A) \times 100$ wherein A is the count for a control group (given physiological saline) and B, for the treated group.

As Table 3 shows, the compound in accordance with the present invention strongly inhibited the production of IgM antibody.

TABLE 3

Inhibition of IgM antibody production
against sheep red blood cells by the
compound of spergualin (trihydrochloride)

| Dose (mg/kg/day) | IgM plaque-forming cell count (cells/10$^6$ spleen cells × 100 ± S.D.) | Inhibition (%) |
|---|---|---|
| 0 (control) | 1,454 ± 197 | 0 |
| 1 | 1,304 ± 188 | 10.3 |
| 5 | 632 ± 87* | 56.5 |
| 10 | 392 ± 87* | 73.0 |
| 25 | 149 ± 53* | 89.7 |

TABLE 3-continued

Inhibition of IgM antibody production
against sheep red blood cells by the
compound of spergualin (trihydrochloride)

| Dose (mg/kg/day) | IgM plaque-forming cell count (cells/10$^6$ spleen cells × 100 ± S.D.) | Inhibition (%) |
|---|---|---|
| 50 | 64 ± 24* | 95.5 |

*significant (P < 0.001)

EXPERIMENT 4

Inhibition of IgG antibody production against Sheep Red Blood Cells by spergualin (trihydrochloride)

CDF 1 mice (6–10 wk old, female) were immunized by intravenous injection of $1 \times 10^8$ sheep red blood cells. The mice were intraperitoneally administered 50 mg/kg/day of the test compound for a period of 4 days starting on the day following the immunization or 3 days after that day. Seven days after the sensitization, spleen cells were isolated and the number of IgG plaque forming cells was counted by a known method (Yata et al., supra). As in Experiment 3, the percentage inhibition of IgG antibody production was determined. The results are shown in Table 4, from which one can see that in either of the two administration schedules, the compound of the present invention exhibited strong inhibitory action on IgG antibody production.

TABLE 4

Inhibition of IgG antibody production
against Sheep Red Blood Cells by spergualin
(trihydrochloride)

| Dose (mg/kg/day) | Administration schedule (days after sensitization) | IgG plaque forming cell count (cells/10$^6$ spleen cells ± S.D.) | Inhibition (%) |
|---|---|---|---|
| control (0) | — | 508 ± 89 | 0 |
| compound of the present invention (50) | 1–4 | 17 ± 16* | 96.7 |
| compound of the present invention (50) | 3–6 | 19 ± 15* | 96.3 |

*significant (P < 0.0001)

EXPERIMENT 5

Inhibition of IgE Antibody Production Against Egg albumin by spergualin (trihydrochloride)

BALB/c mice (7 wk old, female) were challenged by intraperitoneal administration of 10 μg of egg albumin together with 4 mg of aluminum hydroxide gel. Thereafter, the mice were intraperitoneally administered 50 mg/kg/day of the test compound in accordance with the schedules shown in Table 5. After the challenge, blood was drawn from the fundus of each mouse at 10-day intervals for serum collection. The antibody titer of IgE in the serum was determined by passive cutaneous anaphylaxis as follows. Fischer 344 rats (female, 10 wk old) were injected with 0.05 ml of a diluted serum into the dorsal skin. Four hours later, 1 mg of egg albumin and 0.5 ml of 1% Evans blue were injected into the tail vein, and the final serum dilution that produced a blue spot of a diameter of at least 5 mm 30 minutes after the intravenous injection was used as a measure of the antibody titer.

The results are shown in Table 5, from which one can see that the compound strongly inhibited IgE production when it was administered right after the antigenic challenge.

TABLE 5

Inhibition of IgE antibody production against egg albumin by spergualin (trihydrochloride)

| Administration schedule (days after challenge) | Administration times | IgE antibody titer (dilutions ± S.D.) | | | |
|---|---|---|---|---|---|
| | | 10 days | 20 days | 30 days | 40 days |
| Control (untreated) | 0 | 110±85 | 230±124 | 440±339 | 680±497 |
| 1–8 | 8 | 13±33 | 60±31 | 320±0 | 320±0 |
| 9–16 | 8 | 120±98 | 110±106 | 320±0 | 480±392 |
| 1–16 | 16 | 0±0 | 8±9 | 80±120 | 200±131 |

Dose: 50 mg/kg/day (i.p.)

EXPERIMENT 6

Inhibition of Allokiller T-lymphocyte Genesis by spergualin (trihydrochloride)

$3 \times 10^7$ P815 mastocytoma cells were administered intraperitoneally to C 57 BL/b mice (10 wk old). Twelve days later, spleen cels were isolated and used as effector cells (E). Target cells (T) which were $^{51}$Cr labelled P815 mastocytoma cells were challenged by the effector cells at varying E/T ratios and the allokiller activity was assayed in terms of the percentage release $^{51}$Cr. Spergualin was administered for nine consecutive days starting on the day following the transplantation or a single administration was made on the 9th day. As shown in Table 6, the compound of the present invention inhibited appreciably the allokiller activity against the graft.

TABLE 6

Inhibition of Allokiller T-Lymphocyte Genesis by spergualin (trihydrochloride)

| Dose (mg/kg/day) | Administration schedule (days after transplantation) | Percent release of $^{51}$Cr E/T ratio | | |
|---|---|---|---|---|
| | | 5 | 10 | 20 |
| 0 (control) | — | 34 | 48 | 68 |
| 5 | 1–9 | 6 | 8 | 17 |
| 50 | 1–9 | 0 | 0 | 1 |
| 50 | 9 | 21 | 30 | 51 |

E/T ratio: Effector cell (spleen cell)/target cell ($^{51}$Cr mastocytoma)

EXPERIMENT 7

Inhibition of Rejection of Skin Allograft by spergaulin (trihydrochloride)

Skin sections (5×10 mm) were peeled from the tails of SHR rats (female, 10 wk old) and transplanted to Fischer rats (female, 10 wk old) on the back. Varying doses of spergualin were administered intraperitoneally for a consecutive period of 10 or 20 days starting on the day following the transplantation. Complete necrosis of the graft was used as a measure of rejection and the inhibitory action of the compound was evaluated in terms of how long the rejection was postponed. As shown in Table 7, the inhibitory action of the compound was dose-dependent. The longer the period of administration, the greater the inhibitory action. Complete inhibition of the rejection was ensured throughout the administration period. No inhibition of the bone marrow was observed.

TABLE 7

Inhibition of Rejection of Skin Allograft by spergualin (trihydrochloride)

| | Dose (mg/kg/day) | Administration period (days after transplantation) | No. of rats in one group | Average No. of days before rejection (days ± S.D.) |
|---|---|---|---|---|
| Run 1 | Control (untreated) | — | 24 | 7.4 ± 1.3 |
| | 6.25 | 1–10 | 6 | 10.2 ± 2.6 |
| | 12.5 | 1–10 | 9 | 13.0 ± 4.2 |
| | 25.0 | 1–10 | 14 | 14.9 ± 6.9 |
| | 50.0 | 1–10 | 12 | 17.0 ± 3.2 |
| Run 2 | Control (untreated) | — | 5 | 6.6 ± 1.8 |
| | 25.0 | 1–10 | 8 | 15.0 ± 5.2 |
| | 25.0 | 1–20 | 8 | 31.0 ± 1.9 |

EXPERIMENT 8

Delay of graft-versus-host disease in irradiated CBA mice transplanted with C57BL/6 bone marrow cells and spleen cells by spergualin.

Female CBA mice of 9 week-old and female C57BL/6 mice of 9 week-old were used. A group consisted of 10 mice. Bone marrow cells ($10^7$) and spleen cells ($5 \times 10^6$) from CBA mice and C57BL/6 mice were injected i.v. into the whole body irradiation (850 rad) CBA mice. Spergualin was administered i.p. once a day for 10 days starting on one day after the injection of bone marrow cells and spleen cells. The data is indicated as the median survival time.

TABLE 8

Delay of graft-versus-host disease in irradiated CBA mice transplanted with C57BL/6 bone marrow cells and spleen cells by spergualin (trihydrochloride)

| Donor | Dose (mg/kg) | 80-day survivors Survivors/Total | MST (days) |
|---|---|---|---|
| None | 0 | 0/10 | 11.7 |
| CBA | 0 | 10/10 | >80.0 |
| C57BL/6 | 0 | 0/10 | 37.0 |
| C57BL/6 | 3.13 | 2/10 | 33.0 |
| C57BL/6 | 6.25 | 3/10 | 45.3* |
| C57BL/6 | 12.5 | 4/10 | 55.0** |
| C57BL/6 | 25.0 | 9/10 | >80.0** |

*P < 0.05,
**P < 0.01 (t-test).

EXPERIMENT 9

Effect of spergualin (trihydrochloride) on experimental aplastic anemia in mice.

Female C3H/HeN mice (Mls$^c$) of 10 week-old and female CBA mice (Mls$^d$) of 10 week-old were used. A group consisted of 10 mice. CBA lymph node cells ($10^7$) were i.v. into C3H/HeN mice after being subjected to 600 rads of whole-body X-irradiation, spergualin was given i.p. once a day for 10 days. The data is indicated as the mean survival time ±S.D.

TABLE 9

Effect of spergualin (trihydrochloride) on experimental aplastic anemia in mice

| Dose (mg/kg) | 30-day survivors Survivors/Total | MST (days) |
|---|---|---|
| Exp. 1. 0 | 2/10 | 15.1 ± 8.4 |

TABLE 9-continued

Effect of spergualin (trihydrochloride) on experimental aplastic anemia in mice

| Dose (mg/kg) | | Survivors/Total | MST (days) |
|---|---|---|---|
| | 3.13 | 2/10 | 16.3 ± 8.1 |
| | 6.25 | 6/10 | 22.6 ± 9.7* |
| | 12.5 | 10/10 | 30.0 ± 0.0** |
| | 25.0 | 6/10 | 23.6 ± 8.6* |
| Exp. 2. | 0 | 1/10 | 16.2 ± 5.5 |
| | 6.25 | 3/10 | 20.2 ± 8.4 |
| | 12.5 | 6/10 | 23.0 ± 9.4* |
| | 25.0 | 4/10 | 20.7 ± 8.5 |
| | 50.0 | 0/10 | 12.6 ± 3.9 |

*$P < 0.05$,
**$P < 0.01$ (t-test)

EXPERIMENT 10

Effect of spergualin (trihydrochloride) on an acute experimental allergic encephalomyelitis.

Male strain 13 guinea pigs were used. A group consisted of 5 guinea pigs. An aqueous suspension of 50% syngeneic spinal cord homogenate was emulsified in an equal volume of complete Freund's adjuvant containing M. tuberculosis at 20 mg/ml. The antigen emulsion (0.1 ml) was injected both hindfootpads of a guinea pig. Spergualin was administered i.p. for 2 weeks at 0.78 and 1.56 mg/kg.

TABLE 10

Effect of spergualin (trihydrochloride) an acute experimental allergic encephalomyelitis in guinea pigs

| SGL (mg/kg) | Mean survival time[1] (days) |
|---|---|
| 0 | 14.6 ± 1.5 |
| 0.78 | 15.2 ± 1.8 |
| 1.56 | 23.6 ± 9.2** |

[1] with S.D.
**$P < 0.01$ (t-test)

(Advantages of the Invention)

As is clear from the above data, the compound of the present invention has strong inhibitory action on transplantation immune reactions without causing any side effects on the bone marrow. The compound also exhibits strong inhibitory action both on the IgE, IgM and IgG antibody production and on allergics, especially those associated with humoral immunity.

The following Examples are provided for further illustrations of the present invention.

EXAMPLE 1

Thirty parts by weight of a hydrochloride of spergualin was mixed with purified water to make a total of 2,000 parts. The solution was passed through a Millipore filter of GS type for sterilization purposes. Two grams of the filtrate was put into 10 ml vials and freeze-dried to prepared injections each containing 30 mg of the hydrochloride of the compound per vial.

EXAMPLE 2

Granules

An intimate mixture of 50 parts by weight of a hydrochloride of spergualin, 600 parts of lactose, 330 parts of crystalline cellulose and 20 parts of hydroxypropyl cellulose was compacted with a Roller Compactor ®, and ground into particles which were sieved to provide granules of a size between 16 and 60 mesh.

EXAMPLE 3

Tablets

A mixture of 30 parts by weight of a hydrochloride of spergualin, 120 parts of crystalline lactose, 147 parts of crystalline celluolose and 3 parts of magnesium stearate was processed with a V-type pelletizing machine to produce tablets each weighing 300 mg.

We claim:

1. The method for inhibiting the humoral immunity in a mammal having transplanted tissue which comprises administering spergualin or a pharmaceutically acceptable salt thereof by injection or oral administration in effective amount to the said mammal.

2. The method for inhibiting the appearance of allokiller T-lymphocyte in a mammal having transplanted tissue which comprises administering spergualin or a pharmaceutically effective salt thereof by injection or oral administration in effective amount to the said mammal.

3. The method for treating an allergic disease caused by overproduction of at least one selected from a group consisting of IgG, IgM and IgE in mammal having said allergic disease, which comprises administering spergualin or a pharmaceutically acceptable salt thereof by injection or oral administration in effective amount to the said mammal.

4. The method for treating an autoimmune disease which is an allergic encephalomyelitis or an aplastic anemia in mammal having said autoimmune disease, which comprises administering spergualin or a pharmaceutically acceptable salt thereof by injection or oral administration in effective amount to the said mammal.

* * * * *